April 11, 1944. E. W. FREELAND Plant Pat. 623
PEACH TREE
Filed Nov. 4. 1943
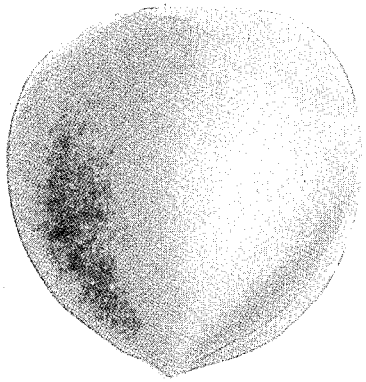
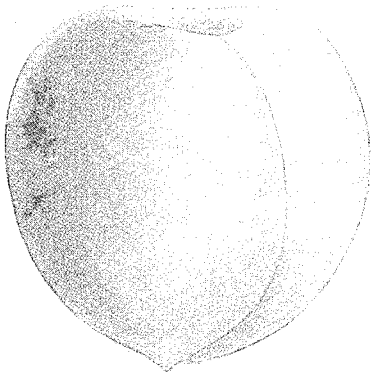
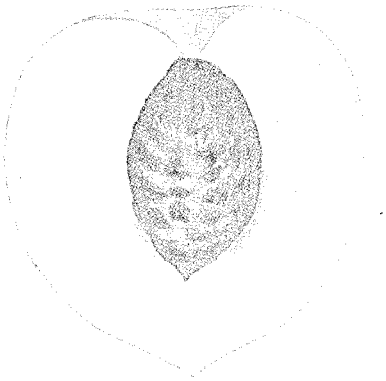
Inventor
Elmer W. Freeland
By Robb & Robb
Attorneys Patented Apr. 11, 1944 Plant Pat. 623

UNITED STATES PATENT OFFICE

623

PEACH TREE

Elmer W. Freeland, Clarinda, Iowa, assignor to Stark Bro's Nurseries and Orchards Company, Louisiana, Mo., a corporation of Missouri Application November 4, 1943, Serial No. 508,966

1 Claim. (Cl. 47—62)

This discovery relates to a new and distinct variety of peach tree, originating as a seedling in my garden.

This new variety has been subjected to prolonged tests, and these have shown that it possesses certain valuable characteristics hereinafter referred to which make it a highly desirable addition or improvement from a commercial standpoint when compared to similar varieties grown under comparable conditions.

The drawing shows two side views and a sectional view of the fruit.

Of primary importance, it appears to be hardy of bud and wood since it survived in one season a drop in temperature over night of 65° while in full leaf, most unusual for peach varieties. That this was not simply an isolated exception in its inherent characteristics was fully demonstrated by its ability, in another instance, to set a crop following a long, severe winter and when a large part of the fruit trees of all kinds in the section where it was growing were heavily damaged or killed outright, it again survived. Notwithstanding the severity of seasons, the original tree of this variety set crops in each of the succeeding years of 1936 to 1941, during which the tests were continued for the purposes of determining this hardiness characteristic, something quite remarkable for the State of Iowa. The buds, furthermore, survived the difficult winter of 1942–43, although, it may be noted, that the frost of the following April did kill the year's crop.

In addition to this hardiness, this new peach takes on excellent color long before it ripens, a good shipping factor, and it is superior to the "J. H. Hale" in quality, while it ripens a week or ten days after "Hale."

A sexual reproduction shows that these characteristics hold true through succeeding propagations.

The following is a detail description of this new variety, color terminology thereof according with dictionary significance. (Observations made at Garden and Atlas, Ill.)

Dates first and last picking: August 22–August 25, at Atlas, Illinois.

Tree: Large; vigorous; medium dense; spreading; hardy; productive; regular bearer.

*Trunk.*—Stocky medium smooth.

*Branches.*—Medium stocky; smooth; olive grayish green; glossy.

*Leaves.*—Length—6 inches. Width 1½ inches. Large; linear; actually pointed; thick and long; medium green; smooth. *Margin.*—crenate; coarsely serrate. *Petiole*—short; medium thick. *Glands*—opposite; medium large; reniform; free.

*Flowers.*—Medium late compared with other varieties; very large; pink.

Fruit: Maturity when described—eating, August 22nd. Hard and highly colored when matured.

*Size.*—Large to medium. Axial diameter—3 inches. Transverse in suture plane—2⅞ inches. At right angles to suture plane—2⅝ inches.

*Form.*—Uniform; symmetrical; globose; sides unequal. *Suture*—distinct; shallow; extends from base to beyond but discontinues at apex. *Ventral surface*—rounded. *Cavity* — rounded. Depth — ¼ inch. Breadth—¾ inch. Markings—radiating red lines. *Base*—rounded. *Apex*—short; mammiform. *Pistil point*—apical.

*Stem.*—Length—⅛ inch. Stout; glabrous.

*Adherence to stone.*—Medium strong.

*Skin.*—Thin; medium tough; free. Tendency to break—none in wet season. Color—highly blushed red. Down—moderate; short; does not roll up when rubbed.

*Flesh.*—*Color*—yellow, mottled with red next to stone. Surface of pit cavity—pink.

*Amygdalin.*—scant. Juice, moderately abundant.

*Texture.*—Meaty.

*Fibres.*—Few; tender.

*Ripens.*—Fairly even.

*Flavor.*—Subacid.

*Aroma.*—Distinct.

*Eating quality.*—Finest or best.

*Stone*: Free. *Fibres*—short; retains short fibre-like threads along ridges.

*Size.*—Small. Length—1½ inches. Width—1 inch. Thickness—¾ inch.

*Form.*—Obovoid toward apex. *Base*—straight; narrow. *Apex* — acuminate. *Sides*—unequal. *Surface*—irregularly furrowed near base toward apex; pitted.

*Ridges.*—Rounded.

*Pits.*—Circular; without wing.

*Dorsal edge.*—Narrow with shallow groove throughout. Ridges on either side—interrupted.

*Use:* Market; local; canning.

*Keeping quality:* Good.

*Resistance:* To insects—medium. To diseases—medium.

*Shipping quality:* Good.

I claim:

A new and distinct variety of peach tree, characterized as to novelty by its unusual hardiness both as to bud and wood, the early coloring of the fruit before ripening, and its superior quality and later ripening period with respect to the "J. H. Hale" variety, substantially as shown and described.

ELMER W. FREELAND.